US012788233B2

(12) United States Patent
Coyle et al.

(10) Patent No.: US 12,788,233 B2
(45) Date of Patent: Nov. 10, 2026

(54) CONTROLLED MOTION CAPSULE

(71) Applicant: Brian Michael Coyle, Canyon, CA (US)

(72) Inventors: Brian Michael Coyle, Canyon, CA (US); Alys Larsen, Canyon, CA (US)

( * ) Notice: Subject to any disclaimer, the term of this patent is extended or adjusted under 35 U.S.C. 154(b) by 481 days.

(21) Appl. No.: 18/534,752

(22) Filed: Dec. 11, 2023

(65) Prior Publication Data

US 2024/0130608 A1 Apr. 25, 2024

Related U.S. Application Data

(63) Continuation-in-part of application No. 17/825,515, filed on May 26, 2022, now Pat. No. 11,883,007.

(60) Provisional application No. 63/230,699, filed on Aug. 7, 2021.

(51) Int. Cl.
*A61B 1/04* (2006.01)
*A61B 1/00* (2006.01)

(52) U.S. Cl.
CPC .......... *A61B 1/041* (2013.01); *A61B 1/00006* (2013.01); *A61B 1/00016* (2013.01); *A61B 1/00097* (2022.02)

(58) Field of Classification Search
CPC ... A61B 1/041; A61B 1/00016; A61B 1/0661; A61B 1/0684; A61B 5/073; A61B 2560/045; A61B 2090/3945; A61F 2210/0047; A61N 5/06; A61N 2005/0651; A61N 2005/0653
See application file for complete search history.

(56) References Cited

U.S. PATENT DOCUMENTS 4,507,115 A * 3/1985 Kambara ............ A61M 31/002 604/93.01
9,750,923 B2 * 9/2017 Niichel .................. A61K 31/00
2005/0096712 A1 * 5/2005 Abraham-Fuchs .... A61B 34/73 607/89
2007/0123809 A1 * 5/2007 Weiss ..................... A61H 21/00 601/84
2008/0188837 A1 * 8/2008 Belsky ................. A61K 9/0097 604/890.1

* cited by examiner

*Primary Examiner* — Michael J Carey
*Assistant Examiner* — William B Chou

(57) ABSTRACT

Controlled motion capsules and associated systems and methods are described. Controlled motion capsules can decelerate, and stop, without damaging epithelial walls. If any components fail, a controlled motion capsule, without added energy, becomes its most compact shape, passing harmlessly through the GI tract. Controlled motion capsule includes a stimuli-responsive hydrogel, comprising a reversible soft copolymer, in a compartment in the capsule, with an energy emitter, and a controller to variably activate energy emission to expand and contract the hydrogel, on detection of certain conditions or instructions. Hydrogel expansion is primarily described by an isotropic tensor, with any deviatoric strains aggregating to a minor degree. The spherically expanded hydrogel decelerates the controlled motion capsule through form drag, and may stop it through viscoelastic interaction with epithelial walls, which avoids damaging friction. Motion control allows scientists to study the microbiome, doctors to deliver intestinal drugs at precise locations, and to closely examine signs of precancerous growth.

17 Claims, 3 Drawing Sheets

CONTROLLED MOTION CAPSULE

CROSS-REFERENCE TO RELATED APPLICATIONS

This application is a continuation-in-part application of U.S. patent application Ser. No. 17/825,515 filed 26 May 2022 which is incorporated by reference as if set forth at length herein, and which claims priority from U.S. Provisional Patent Application Ser. No. 63/230,699 filed 7 Aug. 2021, which is hereby incorporated by reference in its entirety.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

Swallowable endoscopic capsules, which move through the digestive system through the collective actions of digestion, present an alternative to the endoscopic cable probe and camera currently employed in the human health care field. The cable and camera systems demand patient sedation, cause patient discomfort, have potential risks, and are costly. Capsule systems can be used in out-patient settings, cause no discomfort, have little risk, and cost much less. But health care has extraordinary demands. Since their introduction 15 years ago, and despite advances in the field of miniaturization generally, there has been limited use of capsules for routine endoscopic investigation. It is not enough to be less expensive and less invasive. A health care solution must perform as well or better than existing solutions to change health care practice.

The motion of cable and camera endoscopic systems can be controlled by medical practitioners. They can decelerate motion of the device, including stopping it, to examine areas of the body where they detect a condition of interest. This also offers an incomplete degree of camera localization, necessary for diagnosis and prognosis of multiple diseases. Although sensors can increase the precision of absolute position determination, many gastroenterologists prefer the feasibility of estimating the relative position of the camera by measuring from the start of the colon. For example, in "*Motion-based camera localization system in colonoscopy videos*" (Yao et al., *Medical Image Analysis,* 73, 102180, 2021) this is considered sufficient for contextual understanding of colon features.

The control of motion of capsule endoscopes is currently limited. Their movement through the intestinal system is due to peristaltic flow, a non-linear process that varies according to fluid properties (viscosity, thermal volatility and conductivity), wall properties (dimension, absorbency), non-continuum slip flow, chemical actions, microbe distributions, and inclination. Groups of muscle fibers contract in the intestinal wall, squeezing solids and fluids forward towards an area where muscles are relaxed. For example, in "*Peristaltic flow of non-Newtonian fluid through an inclined complaint nonlinear tube: application to chyme transport in the gastrointestinal tract*" (Vaidya, H., et al., *Eur. Phys. J. Plus,* 135, 934, 2020) models of the system emphasize its nonlinear variability. As a force that propels capsule endoscopes, peristaltic flow does not promote locationization specificity. This is the limiting factor against capsule endoscope adoption.

There has been an effort to advance the use of swallowable endoscopic capsules, by increasing the control a medical investigator has of the capsule movement through the internal organs of a patient. For example, in "*Localization strategies for robotic endoscopic capsules: a review*" (Bianchi, F., et al., *Expert Review of Medical Devices,* 16, 5, 2019, pages 381-403) methods are reviewed that attempt to simply locate the capsule accurately, rather than control its movement. Capsules cannot be accurately detected by ultrasound detection, the most cost-effective option.

Several academic and industrial groups have investigated the use of magnetic field-based localization and locomotion strategies. A magnetized capsule that is propelled and directed through a gastrointestinal (GI) tract with external magnetic fields generated on a table the patient lays on was disclosed in U.S. Pat. No. 8,684,010, entitled "Diagnostic and therapeutic magnetic propulsion capsule and method for using the same" granted on Apr. 1, 2014. Its goal is to overcome the limitations of gastrointestinal motility and gravity for movement, the randomness of imagining, and inability to focus on a specific location. The external magnet solution is complex and difficult, since the intervening body tissue reduces magnetic forces, and the intestines are nonlinear, requiring the capsule to move through many degrees of freedom. The goal is to use magnetic fields for capsule steering and locomotion. To move a magnetic capsule through a body requires magnetic forces similar to those found in MRI systems. Biological tissue has almost no magnetic susceptibility. The magnetic pull on the human body will always be less than gravity. However a capsule must be magnetically susceptible to be navigated by a magnetic field. The maximum magnetic gradient on some MM systems can exceed 10 T/m, exerting forces on ferromagnetic objects of 60 to 250 times their gravitational weight. Such a force can accelerate a ferromagnetic object to a speed of 200 km/h in less than 25 milliseconds.

U.S. Pat. No. 9,283,044, entitled "Solenoid system for magnetically guided capsule endoscopy" granted on Mar. 15, 2016, teaches a magnetically guided capsule endoscopy system that can be controlled by a technician, using a table under which a solenoid system emits magnetic fields. It is limited to investigating a patient's esophagus and stomach. FDA has authorized magnetic capsules only for use in the stomach, to keep the capsule in the stomach. This requires much less control than navigation through the GI tract. It has proved challenging to avoid interference between localization and locomotion modules. Because magnetic gradients are steep, capsule movement through the GI tract required forces that continuously vary. Because the orientation of a ferromagnetic object alters its magnetic susceptibility, changing capsule orientation will cause it to be pulled more or less rapidly. To overcome this, a magnetic source can be moved as close to the body as possible in an effort to saturate ferromagnetic capsules. However this will cause the capsule to be dangerously accelerated.

Other methods have been tested to slow or pause capsule movement, for example in "*Modelling and Motion Analysis*

*of a Pill-Sized Hybrid Capsule Robot*" (Huda, M. N., et al., *J. Intel. Robot. Syst.,* 100, 2020, pages 753-764) external "arms," "hooks," and "claws" that rotate out from the capsule to rub against gastrointestinal [GI] tract walls are described. The GI tract is filled with fluid and suspended solids, in a convoluted tubular system. This can impact plastic, composite, or metal appendages sticking out from the sides of a swallowable capsule, causing them to bend or break, or jam into the soft epithelial folds of side walls. Such devices have not been approved by FDA. Any device can fail, so all swallowable capsules must have a configuration that, in case of failure, permits them to safely pass through and out of the GI tract. A device with external elements, should the device fail to rotate or fold them back, presents an unacceptable health care risk.

As these efforts show, there is needed an efficient and effective swallowable capsule device for GI inspection and treatment that can be decelerated and stopped in a specific position in the GI tract, without heavy, dangerous magnetic machinery, without external elements that may break or lodge, without elements that may cause intestinal blockages. The need is exemplified by U.S. Pat. No. 10,300,296, entitled "Capsule phototherapy" granted on May 28, 2019, which is a light-emitting capsule that tries to prevent the inevitable photodynamic damage that will happen when movement of a capsule that emits therapeutic radiation varies unpredictably within a GI tract. Because such capsules cannot adjust velocity, and may stall at any time, this device includes a speed determination unit, which is used to adjust or stop irradiation. This illustrates an effort to mitigate the limitations of lack of capsule motion control. It treats a by-product of swallowable capsule movement, rather than fixing the problem. Current cable and camera endoscopic systems can modify motion to inspect areas of concern. This is the threshold that must be achieved, safely, to achieve capsule success.

Somalocation is herein defined as a three-dimensional spatial position within a body. Only by pausing the movement of the capsule can careful examination occur, can accurate somalocation be determined, can precision therapy be provided. Within the domain of health care, devices must also fail safely. If capsule power, communication, control, or other attributes fail, rendering a capsule inoperable, the capsule must not become a health risk.

SUMMARY OF THE INVENTION

Embodiments of the invention provide devices, systems, and methods for visiting various tubular locations in the body. The embodiments provide a swallowable device that is a controlled motion capsule that contains a shape changing material such as a hydrogel or other gel-like media in a capsule compartment, the shape changing material having the capacity to reversibly expand and contract on exposure to one or more energy emissions. These include radiation that transmits one or a plurality of wavelengths (between 200 nm and 2,000 nm) and which may transmit thermal energy. Particular embodiments provide a swallowable device, in capsule form, for carrying out inspection of tubular structures in the human body, especially the GI tract, as well as delivering therapeutic agents therein. Embodiments provide a gel-like media in the capsule that swells and shrinks, known as a stimuli-responsive hydrogel. Embodiments of the invention are useful for close inspection and medical investigation of the body's tubular structures, by decelerating the controlled motion capsule when the shape changing material expands when exposed to energy emissions, and stopping when when the shape-changing material interacts viscoelastically with the tubular structure's walls. Further embodiments of the invention can be used to deliver therapeutic treatments that require precise somalocation. The controlled motion capsule may have various optical, magnetic, rotational, accelerational, and other sensor signals, used to track its trajectory and determine somalocation.

In one aspect, the invention provides a swallowable device for inspection and treatment of the small or large intestine. The device is a controlled motion capsule that can be swallowed and pass through the GI tract. The controlled motion capsule includes an external shell and an interior volume and can be made from various polymers known in the art. The controlled motion capsule can include at least one component in which a gel-like media such as a hydrogel or liquid crystal elastomer is positioned, which can reversibly swell and shrink, or reversibly change from one shape to a different shape. Hydrogels are three-dimensional polymer networks that can swell due to hydration. Hydrogels have chemical or physical crosslinks. The crosslinks produce changes in hydrogel viscoelastic properties. Many hydrogels can reversibly swell and shrink in response to changes in external environmental stimuli, and those with physical crosslinks possess physical domain junctions, hydrogen bonding, hydrophobic interaction, and ionic complexation, facilitating fabrication and reshaping, and exhibit superior biodegradation and non-toxicity.

Hydrogels with different concentrations of water-soluble synthetic polymers exhibit different network structures, with different responses to light and temperature induced phase transitions. Light-responsive hydrogels include photopolymerizable hydrogels, where light adds crosslinks and/or biochemical cues, and photolabile hydrogels where light cleaves crosslinks and/or removes biochemical cues and/or caging compounds. Photo-sensitive molecules respond to light via several main mechanisms. This invention has embodiments that use isomerization or cyclization, degradation, and dimerization of constituent compounds. Embodiments include hydrogels tuned to optimize texture and wavelength response. Viscosity modifiers may be added to the media, such as carboxylic acids or polyhydric alcohols. Mechanical properties may be improved by interlacing multiple inseparable polymer networks that do not covalent bond with each other. Embodiments include a controlled motion capsule with a hydrogel that expands spherically into an internal body tube, and decelerates the capsule's motion via form drag. Form drag arises because of the shape and size of the hydrogel. Higher pressure forms on the forward motion side of the hydrogel than the back of the hydrogel, if immersed in fluid. This decelerates capsule movement, following Bernoulli's principle. Embodiments include a controlled motion capsule with a hydrogel that interacts with luminal walls to stop capsule motion using viscoelastic interactions. The hydrogel dissipates mechanical energy to viscous effects. The lumen in also viscoelastic. Its main structural component is an extracellular matrix that is essentially a hydrogel: a polymeric network with interstitial liquids. When two viscoelastic objects interact they decelerate more efficiently than purely elastic or static bodies. The main collision takes place in the soft, fluid-like layers, where energy is transferred via deformation. This stops the capsule without using friction.

"Positive" light-responsive or thermo-sensitive hydrogels swell at high temperatures or under irradiation, and shrink at low temperatures or in the absence of light. "Negative" light-responsive or thermo-sensitive hydrogels swell at low temperatures or in the absence of light, and shrink at high temperatures or under irradiation. In this invention's embodiments, "positive" light-responsive or thermo-sensitive hydrogels are preferred, to provide a fail-safe mechanism for ensuring the device will shrink to a compact form should device components, such as energy sources or controls, fail. This is because when the energy sources or controls cease, the "positive" hydrogel shrinks, and any surrounding membrane contracts. Such embodiments ensure the passage and excretion of the device through the GI tract.

Embodiments may incorporated one of more of the following photoactive components in the hydrogel matrices: photocleavable groups, photothermal agents, molecular photoswitches. These tune physical, chemical, and biological properties of the hydrogel. Embodiments may incorporate molecular photoswitches, such as azobenzenes, diarylethenes, stilbenes, spiropyrans, and their derivatives. These reversibly reconfigure hydrogel conformations when irradiated. Embodiments may use merocyanine dyes that convert to spiropyran moieties when exposed to visible light. Embodiments may contain sulfonate-based groups incorporated into cross-linked polymer networks. Silk fibroin and homologous proteins may be incorporated in the hydrogels of this invention. These may facilitate adhesion to luminal surfaces.

An embodiment includes light-responsive hydrogels formed by incorporating spiropyran chromophores that are copolymerized with poly(N-isopropylacrylamide) and polyacrylic acids. Another embodiment forms copolymers of N,N-dimethylacrylamide (DMA) and methacryloyloxyazobenzene (MOAB) with pendant azobenzene chromophore moieties along the backbone. This embodiment may be controlled with light at 430-436 nm. Another embodiment uses hexaarylbiimidazole chromophores directly incorporated into polymer backbones by nonfree radical polymerization.

An embodiment uses peptide amphiphiles (PA) for copolymerization of high-aspect-ratio supramolecular nanostructures to create mechanically robust hydrogels. This is important in reinforcing hydrogel structures, to ensure they remain coherent upon volumetric change. High-aspect-ratio supramolecular polymer reinforces hydrogels by physical entanglement yet maintains a relatively loose crosslinked network that is water permeable, increasing robustness as well as accelerating actuation response to energy inputs. An embodiment uses methacrylamide groups as PA. Embodiments incorporate stimuli-responsive groups such as spiroyans or azobenzenes to cause robust hydrogels to be energy-responsive.

An embodiment incorporates a second hydrogel, which expands anisotropically, within or proximate to a first hydrogel that expands spherically. The first and second hydrogels differ due to the weight percentage of the high-aspect-ratio supramolecular components. In an embodiment the second hydrogel incorporates a charge-transfer (CT) complex of two or more molecules, or of different sections of one large molecule, where a fraction of electronic charge is transferred between different sections of the aggregate. The second hydrogel incorporates stimuli-responsive groups and expands under energy inputs in shapes that resemble membranes or rods. In an embodiment the CT second hydrogel forms a membrane around the first spherical hydrogel. In a further embodiment, the second hydrogel is a thin layer that encapsulates the first hydrogel and expands at least as fast as the first hydrogel. The second hydrogel bends in a geometric manner, forming a shell-like surface. In an embodiment the second hydrogel forms a rod that may press on the spherical hydrogel, permitting increased control of capsule navigation. An external operator or automated operator communicates navigation determinations to the capsule controller, which variably energizes the first hydrogel that expands isotropically, and variably energizes the second hydrogel which expands anisotropically. In embodiments incorporating a second hydrogel, stimuli used to induce at least the second hydrogel's shape change may include one or more of the following: photoactivation, electronic charge, thermal energy.

In general, an implementation generates macroscopic shape change of the material by incorporating molecular photoswitches such as spiropyrans, diarylethenes, hexaarylbiimidazoles, and azobenzenes into the polymer material, and initiating a photochemical reaction with light. Photoisomerization of molecules causes a generally reversable structural change between isomers by photoexcitation. Of the different photoisomerizers available, spiropyrans exhibit extraordinary sensitivity to photons, and are used in preferred embodiments of the invention. The spiropyran photochemical reaction involves dissociation of $C_{spiro}$—O bond followed by either relaxation back to a ring-closed form, or a twisting motion to a new geometry along the pi-electron dimension. It is used in embodiments where the reversibly swelling and shrinking gel-like media is a light-responsive, spiropyran-functionalized hydrogel that is reversibly photoactuated.

Thermo-sensitive hydrogels can be synthesized from natural polymers (chitosan, cellulose, and gelatin) and synthetic polymers (poly[N-isopropylacrylamide] and polyfluorene). In an embodiment a gel-like media may comprise a reversible copolymer containing a derivatized acrylamide in an amount sufficient to cause a transition from a first state to a second state due to a temperature change of less than 25 degrees. The invention may employ coelectrospinning of precursor polymers to create cross-linked nanostructured hydrogels, that reversibly respond to temperature changes within seconds.

Light-activated hydrogel volume changes may be induced by light radiation between 200 and 700 nm, from the near ultraviolet to visible red. Thermo-sensitive hydrogel volume changes may be induced by radiation up to 2000 nm. Ionizing wavelengths are shorter than 125 nm, and are not used. An embodiment incorporates sulfonate-based water-soluble photoswitches that induce volumetric hydrogel expansion upon exposure to nonionizing radiation, and contract under darkness, in a reversable process. Modifying pH and the critical solution temperature of constituent polymers during hydrogel preparation allows expansion and contraction parameters to be explicitly tuned. In an embodiment, the nonionizing radiation is a blue light with a wavelength 405 nm, which causes spiropyran and merocyanine to interconvert, given the hydrogel has acrylic acid merocyanine incorporated. Under light irradiation, the acidic internal gel environment quickly and completely converts the hydrophilic merocyanine to the hydrophobic spiropyran, allowing rapid swelling of the gel from a first to a second condition in less than 90 seconds. Another embodiment prepares the hydrogel by dissolving spiropyran monoacrylate in dimethyl sulfoxide to form a water-soluble photoswitch. This also has volumetric expansion on exposure to photons, and contraction under dark conditions. In a related embodiment, light can be used to reversibly control the association between a photoswitchable azobenzene guest and an α-cyclodextrin host. This supramolecular cross-link interaction causes reversible expansion and contraction of the hydrogel when irradiated.

An embodiment uses photochromic compounds and photochromic moieties other than azobenzenes and spiropyrans to incorporate in the media, such as diarylethenes, spirooxazines and thiospiropyrans, sulfonated spiropyrans, fulgides, diarylethenes, stilbenes, bisimidazols, spirodihydro-indolizines, quinines, fulgide, dithienylethene, hydrazines, anils, thiosulfonates, hexaarylbiimidazoles, azotolene, imines, coumarins, and nitrobenzyls, and similar substances as these, their moieties, derivatives of these, and mixtures thereof. The photochromic materials are selected depending on their compatibility with the polymer matrix, their activation and response rates, and other conditions required of the gel-like media. Peptide crosslinkers containing enzymatically degradable groups and a photoreactive group can form useful chemical patterns. The stiffness and stretchiness of embodiments can be modifying with different monomer lengths and concentrations in the network, and also by changing the concentration of linkers in the prepolymer solution.

In another embodiment, the gel-like media used to control capsule motion incorporate liquid crystal polymers. In an embodiment, nonionizing radiation causes surface strains in three-dimensional liquid crystal polymers, reshaping them. Crosslinked liquid crystalline polymers create alignment layers and alignment structures when exposed to light. These structures, composed of rigid and flexible parts, align mesogen moieties in one direction to form rod or disk shapes. They can be transformed between a nematic phase, the most fluid liquid crystalline state, and smectic or columnar phases, both more ordered and less fluid, forming rod and disk shapes, respectively. Their incorporation in hydrogels can form materials with macroscopic spring-like properties. In an embodiment, light induces expansion, bending, and helical shapes. The mechanism of shape transformation may be based on selective absorption of light of a specific direction. Photochromic moieties in side chains along polymer backbones can act as both mesogens and photoresponsive groups. Because they can form distinct shapes, an embodiment can use liquid crystal polymeric materials to modify the hydrogel shape to form 3D geometries that may press against to luminal surfaces.

Existing materials proposed for operating capsular endoscopes, such as in opening portals or bending appendages, undergo generally planar or anisotropic change. Shear stress is the driving force behind the activation process which allows the polymer chains in these materials to transition to a new, plastically deformed configuration. The shear strain rate is called the deviatoric part of these materials viscous stretching. Deviatoric strains dominate their strain tensor. In this invention, the polymer fraction of the gel-like media has an expansion gradient tensor primarily composed of an isotropic strain tensor. Any deviatoric strains aggregate to less than the isotropic strain. This invention's expansion gradient tensor $F_{GEL}$ is separated into isotropic and deviatoric parts, in which the ratio of isotropic to deviatoric strains is always greater than 1, as in Equation 1.

$$F_{GEL} = \frac{FI}{f} > 1 \qquad \text{Equation 1}$$

F represents the isotropic part of the tensor, spherical deformation due to swelling, and f is the deviatoric part, deformation due to shearing. I is the identity matrix of F spatial dimensions. $f_{ij}$ is <<1 for all ij; the deviatoric part is always less than the isotropic part. Deviatoric strains can be induced internally by differential swelling, but remain small relative to this same (locally) isotropic swelling state. This has important consequences. First, as the shape-changing gel's structure expands isotropically, it remains coherent, as the distribution of deviatoric strains are too small to undermine structure. The coherent spherical expansion of a structurally robust hydrogel functions without a surface cover, such as a membrane. However in a further embodiment, deviatoric strains may be isolated in at least one anisotropic hydrogel matrix, forming an expansion gradient tensor $F_{GEL}^*$ that provides configurations such as a surface cover for the spherically expanded hydrogel, or a tube that presses against the isotropic part. In these configurations equation 1 is not applicable.

An embodiment may include at least one hydrogel in a capsule compartment surrounded by capsule shell, in which the capsule shell is axially slidable relative to the hydrogel compartment; the capsule shell slides to at least one side relative to the hydrogel compartment to allow the hydrogel to expand. An embodiment may include at least one hydrogel in a capsule compartment at one end of the capsule, the hydrogel being at least on one side surrounded by a container; the container being movable may open to allow the hydrogel to expand.

At least one energy emitter is disposed in close proximity to at least one hydrogel in a compartment in the capsule. In an embodiment emitters are in the form of at least one energy source next to the one side, and at least one energy source next to the opposite side, of the compartment, and able to energize the hydrogel as it swells and shrinks. Energizing may be continuous, periodic, pulsate, or follow other duty cycles. A transparent surface may protect each energy source. In an embodiment, when the hydrogel swells it causes energy emitters to move and remain in optimal communication with the hydrogel. When emitters reduce or cease radiation, the hydrogel shrinks and emitters remain positioned within the hydrogel.

In an embodiment at least one energy emitter is positioned on the side of the hydrogel compartment, energizing the hydrogel when activated. In an embodiment emitter energy is projected out of the compartment, in the direction of the hydrogel swelling motion.

An implementation of the controlled motion capsule may include data from at least one sensor on or close to the surface of the controlled motion capsule body, a positioning program module that processes the sensor data, and a controller that activates and deactivates the nonionizing emitters proximate to the reversibly swelling and shrinking gel-like media; data from the at least one sensor is used by the positioning program to calculate the velocity, deceleration, acceleration, slew, turns, and cessation of movement of the controlled motion capsule, incrementally and by time segments; the results of this calculation identify a trajectory and locate the controlled motion capsule's somalocation. In an embodiment the somalocation may be used by an external operator to determine at least one value which is used to execute an intensity and/or duration of emitter activity. The device also includes a power source for providing power to emitters.

In accordance with a preferred embodiment, the controlled motion capsule includes at least one controller that monitors the data, such as data of a dynamic parameter from the interior of a body tubular structure, and determines at least one value, such as a set of values for each data monitored, and wirelessly transits the at least one value to an external operator who determines at least one direction for the controlled motion capsule, that may include its deceleration or movement cessation, and wirelessly transmits the at least one direction to the controller, the controller is coupled to at least one energy emitter and is configured to execute programmed instructions stored in memory including activating the at least one energy emitter according to intensity, duration, and/or duty cycles of energy emissions to achieve the at least one direction, the controller further determining a change in the intensity, duration, and/or duty cycles of energy emissions due to feedback about the dynamic condition of the shape changing materials, the controlled motion capsule somalocation, and/or the local body tubular system, to maintain the at least one velocity.

In a preferred embodiment camera systems provide a plurality of image data wirelessly transmitted to the external operator. Camera systems may provide data that can be used by an image processing program to compare an optical flow field with a background (predetermined or computed) optical flow field, and thereby estimate the position and/or velocity of the camera motion. In an embodiment using optical flow fields and/or optical field patterns, an adaptive threshold may be used to avoid false positives in visual measurements. The image processing program may be in a device the operator controls, separate from the capsule. The image processing program may be partly or wholly within the capsule. An embodiment may use at least one other data to determine capsule position and velocity. The at least one other data includes one or more of the following 1) membranes covering the gel-like media that are connected to the controlled motion capsule and may transmit membrane expansion rates and frictional data to the controller; 2) single and multiple axis accelerometers that may be used to detect the magnitude and the direction of acceleration/deceleration, as well as orientation, vibration, and shock data (micromachined microelectromechanical systems (MEMS) accelerometers may be preferred); 3) miniaturized magnetometers may be used to determine absolute direction of motion; 4) MEMS gyroscopes may be used to detect and measure the rotation rate and pose of the controlled motion capsule; 5) one or more sensors may used, such as a motion sensor that detects movement data of the controlled motion capsule. Sensors may include sensing materials with stimuli response (light, humidity, mechanics, etc.) and multiple detection features; 6) environmental gauges may be used, to assess the temperature, pH, electrostatic charge, and/or moisture level data within the tubular structure surrounding the capsule; and 7) spectral and hyperspectral imaging may be used to detect microbial population distribution and volume data.

The controller may include a timing system to process the controlled motion capsule's position and orientation in the body tubular structure. The controlled motion capsule may operate automatically, the device activating the reversibly swelling and shrinking media according to programmed instructions. As previously stated, precise position and duration of presence are key factors in the controlled motion capsule's success. The device can include a transceiver to send data to, and receive input from, an external resource, such as a human operator or a processor, and this external resource may activate the energy emissions, thereby causing a response in the reversibly shape-changing material. The human operator or the external processor may use observation methods that include, but are not limited to, the methods of ultrasound, x-rays, and/or another sensing or viewing system.

In an embodiment, the controlled motion capsule sensors may detect when conditions of the tubular structure, such as the GI tract, deviate outside of predetermined ranges or conditions, such as pH, temperature, size, and/or microbial populations. In response the controller can activate the reversibly shape-changing material to decelerate and/or stop the controlled motion capsule. In an embodiment a wireless communicator can notify the external operator of the conditions detected, and the position, velocity, and status of the controlled motion capsule. Under predetermined parameters, or in response to the external operator's commands, the controlled motion capsule can remain in a certain location until it receives a signal. Embodiments incorporate a fail-safe system to prevents this from causing intestinal blockage. In an embodiment the controlled motion capsule has recording systems on-board to record visual, chemical, electrophysiological, and/or other data of the environment the controlled motion capsule is located in. In an embodiment one or more of the controlled motion capsule data recodings are transmitted to an external device for storage and autonomous or external operator monitoring. In an embodiment these recording systems are automatically configured to operate under specific conditions, such as when the controlled motion capsule decelerates and/or stops movement in response to the detection of conditions outside predetermined ranges or conditions. In an embodiment the recording systems are configured to operate when the controlled motion capsule decelerates and/or stops movement at certain locations in the tubular structure, such as GI tract. Other methods of triggering the recording systems include an external operator's decision, or via a periodic or stochastic activation function. In an embodiment the controlled motion capsule releases therapeutic compounds in response to sensor data of predetermined conditions, specific locations, and/or input from external agents. The reaction of the environment around the controlled motion capsule to the therapeutic compound release can be monitored and recorded. In this way, therapy impact can be precisely monitored while the controlled motion capsule has ceased movement.

In an embodiment, the controlled motion capsule may stop in a position where it does not cause intestinal blockage. In this position the controlled motion capsule can provide therapeutic treatment over an extended time frame. The advantage of controlling capsule movement is that the capsule can be used at specific times. For example, it can provide stimulation that induces intestinal secretions and/or provide stimuli that increase or decrease microbial activity. It can do so at times that correlate with circadian rhythms, which is important in some disease treatments.

Further details of these and other embodiments and aspects of the invention are described more fully below with reference to the accompanying figures. Reference in this specification to "an embodiment" or "a further embodiment" or similar language means that a particular property, attribute, or structure of the embodiment may be included in at least one embodiment of the present invention. The term "embodiment" as it appears throughout this specification does not necessarily refer to the same embodiment. The properties, attributes and structures described can be combined in one or more embodiments in any suitable way. One skilled in the art will recognize that the invention may be practices without one or more of the specific properties, attributes and structures, or with other properties, attributes and structures.

BRIEF DESCRIPTION OF THE FIGURES

The present invention will be understood and appreciated more fully from the following detailed description taken in conjunction with the drawings in which.

DETAILED DESCRIPTION

It will be readily understood that the components of the present invention, as described and illustrated herein in the figures, can be arranged and designed into a wide variety of different configurations. Therefore, the following detailed embodiments of the systems and methods of the present invention as illustrated in the figures is not intended to limit the scope of the claimed invention, but rather is intended to be representative only of selected embodiments.

Figure 1A:
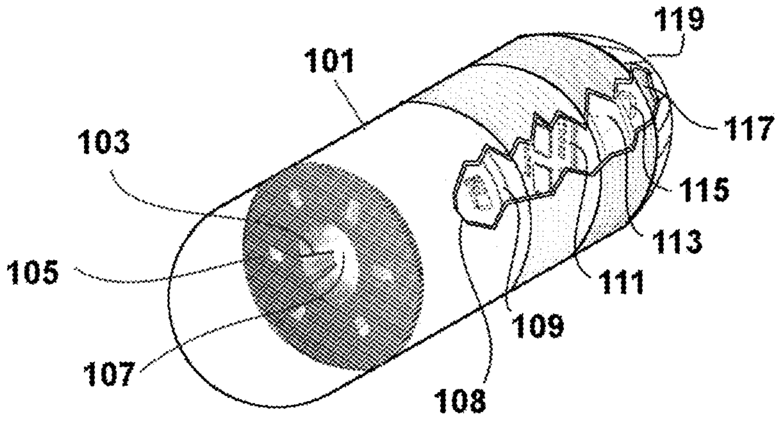
FIG. 1A illustrates a controlled motion capsule device that contains multiple functional components, including a condensed hydrogel.

In FIG. 1A the controlled motion capsule 101 incorporates a sensor 103, light sources 105, and an image recorder 107. In cutaway 108 are shown the following components: transceiver 109, controller 111, battery 113, energy emitter 115 and hydrogel 117. The position of each of these components need not be in this order, or some may be positioned alongside each other. If a wireless transceiver is not used, an archival memory may be used; the archival memory may be used along with a wireless transceiver. Controller 111 supports image recorder 107 processing, including image compression; transceiver 109 transmissions; receives sensor 109 data, and controls lights 105 and energy source 115. A container 119 encloses the hydrogel 117.

Figure 1B:
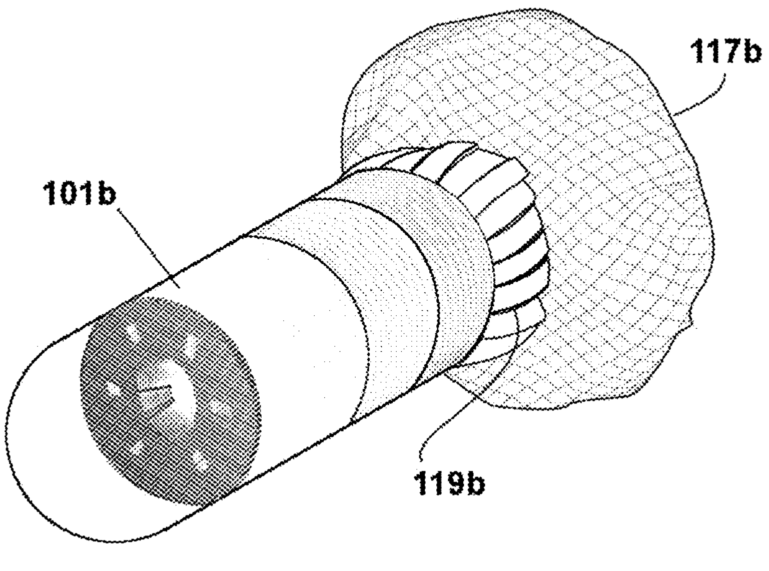
FIG. 1B illustrates a controlled motion capsule wherein a hydrogel is in an isotropic expanded state.

FIG. 1B illustrates an example of the controlled motion capsule 101*b* with the hydrogel 117*b* expanded spherically, its strain tensor predominantly isotropic, and the container 119*b* opened.

Figure 2:
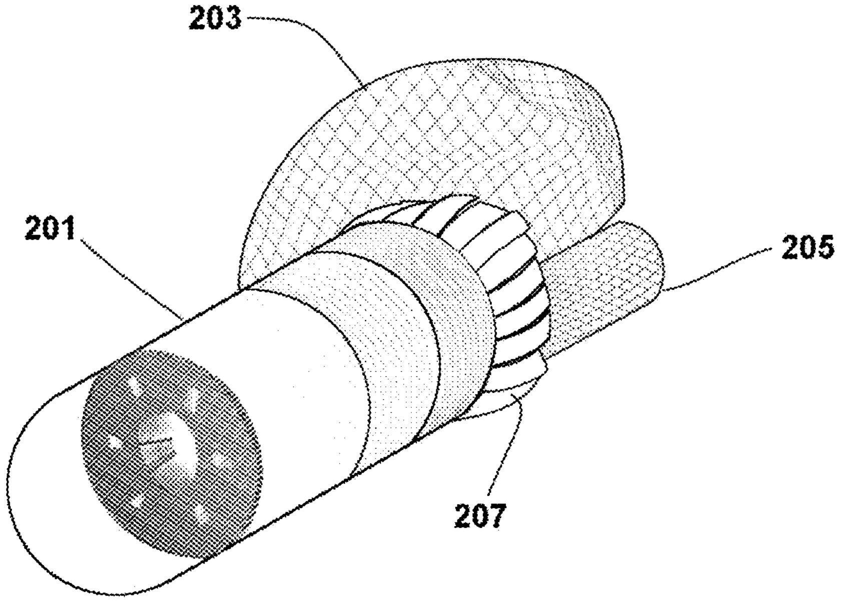
FIG. 2 illustrates a controlled motion capsule wherein a first hydrogel is in an isotropic expanded state and a second hydrogel is in an anisotropic expanded state.

In FIG. 2 the controlled motion capsule 201 is illustrated in an implementation wherein a first hydrogel 203 spherically expands, and a second hydrogel 205 anisotropically expands, and are arranged side-by-side. The container 207 surrounding the hydrogels has opened. The use of two hydrogels allows refined navigation. For example, FIG. 2 illustrates the second anisotropically expanding hydrogel 205 pushing the first spherically expanding hydrogel 203 to one side. This increases the potential of the first hydrogel 203 contacting the luminal surface on that side. The second anisotropically expanding hydrogel 205 may have a predetermined set of functions that each cause the spherically expanding hydrogel 203 to be displaced, thereby changing the capsule 201 motion. The controller is configured to activate energy emissions to produce the functions of the second anisotropically expanding hydrogel 205. One or more embodiments of the present invention may comprise different energy emissions for the first hydrogel 203 and the second hydrogel 205. This may include an phototonic energy emission for the first hydrogel 203, and a charge-based energy emission for the second hydrogel 205. There may be separate controllers for each hydrogel.

Figure 3A:
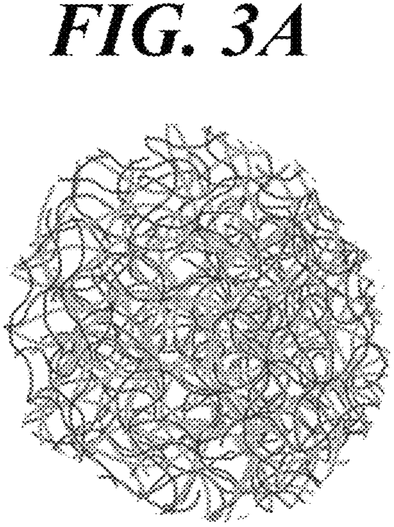
FIG. 3A is a molecular representation of a covalent polymer hydrogel matrix.
Figure 3B:
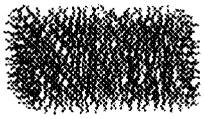
FIG. 3B is a molecular representation of an high-aspect-ratio peptide amphiphile.
Figure 3C:
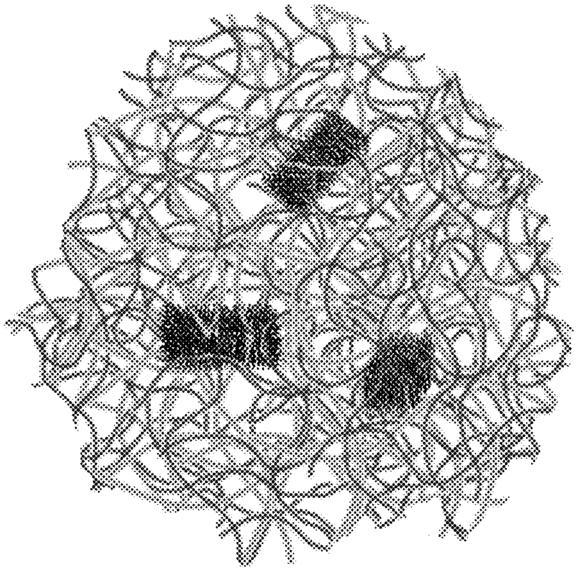
FIG. 3C is a molecular representation of a hybrid polymer hydrogel matrix that incorporates high-aspect-ratio peptide amphiphiles.

Molecular representations are shown in FIG. 3A, FIG. 3B, and FIG. 3C, to illustrate the copolymerization of a polymer hydrogel matrix with peptide amphiphiles that form high-aspect-ratio supramolecular nanostructures. FIG. 3A illustrates a polymer hydrogel matrix without supramolecular nanostructures. FIG. 3B illustrates a high-aspect-ratio supramolecular nanostructure. By changing the peptide sequence during nonstructure assembly, different morphologies can be produced. FIG. 3C illustrates a hybrid system where the hydrogel matrix has supramolecular nanostructures incorporated in the covalent network. The presence of supramolecular nanostructures in the hybrid system does not inhibit the photoisomerization of the photoactive components such as spiropyrans that cause hydrogel expansion. The supramolecular nanostructures reinforces the hybrid system by physical entanglement with the matrix, yet maintains cross-link flexibility highly permeable to water. This causes the expanded hydrogel to be robust and coherent, and causes rapid expansion.

Other molecular compounds may be integrated in the hydrogels of this invention, to increase their response to stimuli, or impart biophysical attributes that enhance navigational control.

An embodiment of the present invention in which an external operator navigates a controlled motion capsule can be based on program codes executed in the on-board controller or transmitted wirelessly to the controller from a processor that executes program codes outside the body. These or other processors can be configured to perform particular tasks that combine to cause the controlled motion capsule to move in a body tube in a manner that conforms to the external operator's instructions.

A "hydrogel" is a hydrophilic three-dimensional (3D) network that is chemically crosslinked or physically entangled with excellent water swelling capacity.

"Gel-like media" is defined herein as any soft material that mimics some of the biochemical and biophysical properties of soft tissue, and includes stimuli-sensitive systems with dynamic responses to light and temperature triggers.

"At least one of A and B" should be understood to mean "only A, only B, or both A and B."

"Selected from the group of A, B, and C" should be understood to mean "only A, only B, only C, or both A and B, or both A and C, or both B and C, or A, B, and C."

"At least one selected from one or more of A, B, C, and D" should be understood to mean "only A, only B, only C, only D, or both A and B, or both A and C, or both A and D, or both B and C, or both B and D, or both C and D, or A, B, and C, or A, B, and D, or A, C, and D, or B, C, and D, or A, B, C, and D."

As used herein, an element or step recited in the singular and proceeded with the word "a" or "an" does not exclude plural of said elements or steps, unless such exclusion is explicitly stated. References to an "embodiment" do not exclude the existence of additional embodiments that also incorporate the recited features. Embodiments "comprising," "including," or "having" an element (component, part) or a plurality of elements (components, parts) having a particular property may include additional such elements not having that property. Ordinal numerals or ordinal number words are used as labels, and are not intended to impose numerical requirements or a particular positional order on their objects.

It will be appreciated by persons skilled in the art that the present invention is not limited to what has been particularly shown and described herein above. Rather the scope of the present invention is defined only by the claims which follow.

The invention claimed is:

1. A controlled motion capsule comprising:
a swallowable case, containing:
at least one image recorder recording at least one visual data;
a controller;
a compartment enclosing a hydrogel;
the hydrogel, comprising a reversible component with at least one hydrophilic component, being capable of expansion;
the hydrogel expansion composed of a generally isotropic strain tensor and none, one, or a plurality of small deviatoric strains;
the none, one, or the plurality of small deviatoric strains, in aggregate, being less than the isotropic strain tensor;
at least one energy emitter proximal to the hydrogel;
an external operator;
a transceiver wirelessly transmits the at least one visual data;
the external operator receiving the at least one visual data;
wherein, if the external operator determines that the controlled motion capsule is in a first condition, the external operator wirelessly transmits at least one signal;
the controller receiving the at least one signal;
wherein, based on the at least one signal, the controller variably energizes the at least one energy emitter to at least one level of energy emission;
the hydrogel expanding and contracting to a volume dependent on the at least one level of energy emission;
wherein motion of the controlled motion capsule through a tubular structure in an animal is variably decelerated by the expansion and contraction of the hydrogel volume.

2. The controlled motion capsule of claim 1, wherein:
the hydrogel contains at least one or more of the following photoactive components in at least one matrices: photocleavable groups, photothermal agents, molecular photoswitches.

3. The controlled motion capsule of claim 2, wherein:
one or more sulfonate-based groups incorporate in the at least one matrices of the hydrogel.

4. The controlled motion capsule of claim 1, wherein:
peptide amphiphiles copolymerize a plurality of high-aspect-ratio supramolecular nanostructures in the hydrogel matrices.

5. The controlled motion capsule of claim 1, wherein:
one or more fibrous proteins incorporate in the at least one matrices of the hydrogel.

6. The controlled motion capsule of claim 1, wherein:
an operational program automatically determines the controlled motion capsule is in the first condition, wherein the operational program communicates the at least one signal to the controller.

7. The controlled motion capsule of claim 1, further comprising:
the transceiver wirelessly transmits at least one biophysical data that describes a sensor measurement, recorded by a sensor in the controlled motion capsule.

8. The controlled motion capsule of claim 7, wherein:
the at least one biophysical data describes one or more of the following: at least one physiological measurement data; at least one capsule physical location measurement data; at least one capsule orientation measurement data.

9. The controlled motion capsule of claim 7, wherein:
the at least one biophysical data is received by the controller.

10. The controlled motion capsule of claim 1, wherein:
the expansion of the hydrogel volume induces form drag that decelerates the controlled motion capsule motion in the tubular structure.

11. The controlled motion capsule of claim 1, wherein:
the hydrogel volume expands to interact viscoelastically with a luminal wall of the tubular structure to stop the controlled motion capsule motion in the tubular structure.

12. A controlled motion capsule comprising:
a swallowable case, containing:
at least one detection system;
the at least one detection system transmitting at least one data;
a controller;
at least one compartment encloses a first hydrogel and a second hydrogel;
the first hydrogel capable of expansion that is primarily composed of a generally isotropic strain tensor;
the second hydrogel capable of expansion that is primarily composed of at least one deviatoric strain tensor;
at least one energy emitter proximal to the first hydrogel and to the second hydrogel;
wherein, if the controller energizes the at least one energy emitter the first hydrogel expands in a generally spherical shape;
wherein, if the controller energizes the at least one energy emitter the second hydrogel expands in a generally anisotropic shape.

13. The controlled motion capsule of claim 12, wherein:
the controller communicates the at least one data to an operator;
the operator determines a first navigation of the controlled motion capsule;
the operator communicates the first navigation to the controller;
the controller variably energizing the at least one energy emitter;
the spherical expansion of the first hydrogel and the anisotropic expansion of the second hydrogel cause the controlled motion capsule to move in the first navigation.

14. The controlled motion capsule of claim 12, wherein:
the operator communicates a first signal to the controller;
the second hydrogel forms a thin surface;
the second hydrogel encapsulates at least a part of the first hydrogel;
in response to the first signal, the controller variably energizing the first hydrogel and the second hydrogel;
the anisotropic expansion of the second hydrogel is at least as fast as the spherical expansion of the first hydrogel;
the second hydrogel forms a surface around the first hydrogel.

15. A system to control the motion of a capsule inserted into a body tube comprising:
a capsular body having an outer shell;
a plurality of compartments formed in the capsular body;
at least one compartment including at least one polymer network that absorbs and retains liquid;
the at least one polymer network having reversible mechanical three-dimensional properties that are responsive to at least one energy stimuli;
an energy source producing the at least one energy stimuli proximal to the polymer network;

wherein the at least one polymer network expands in a spherical three-dimensional manner defined by an isotropic strain tensor greater than a deviatoric tensor in response to the at least one energy stimuli;

the at least one polymer network when expanding reduces the velocity of the capsule in the body tube.

16. The system of claim 15, wherein:

wherein the capsular body outer shell is axially slidable relative to the at least one compartment that includes the at least one polymer network, to allow the at least one polymer network to expand.

17. The system of claim 15, wherein:

wherein the at least one compartment including the at least one polymer network is located at one end of the capsule, and is on at least one side composed with a movable container that opens to allow the at least one polymer network to expand.

* * * * *